United States Patent [19]

Terry et al.

[11] 4,149,532
[45] Apr. 17, 1979

[54] CEREBRAL PALSY ARM AND HAND BRACE

[76] Inventors: Thomas E. Terry, 204 E. Athey, R.R. #1, Farber, Mo. 63345; Laurance J. Hoyt, Sr., R.R. #2, Laddonia, Mo. 63352

[21] Appl. No.: 754,536

[22] Filed: Dec. 27, 1976

[51] Int. Cl.² ............................................... A61F 5/10
[52] U.S. Cl. .................................................. 128/77
[58] Field of Search ............... 128/77, 80 F, 87 R, 128/88; 3/12.2, 1.1, 1.2

[56] References Cited

U.S. PATENT DOCUMENTS

| | | | |
|---|---|---|---|
| 2,010,328 | 8/1935 | Siebrandt | 128/88 |
| 2,362,383 | 11/1944 | Lendinara | 128/80 F |
| 2,832,334 | 4/1958 | Whitelaw | 128/77 X |
| 3,528,413 | 9/1970 | Aydt | 128/88 |
| 3,769,636 | 11/1973 | Friedman | 3/1.1 |

OTHER PUBLICATIONS

"The Engineer" pp. 162-163, 1966.

*Primary Examiner*—Robert W. Michell
*Assistant Examiner*—Michael H. Thaler
*Attorney, Agent, or Firm*—Thomas M. Scofield

[57] ABSTRACT

An arm and hand brace for persons afflicted with the neuro-muscular tremors of cerebral palsy; a bracing device framing the shoulders, upper arm, forearm and hand which, in application, damps and controls involuntary neuro-muscular spasms and permits the performance of controlled, willed actions of these members by cerebral palsy victims; an articulated frame comprised of a support, a train of linked arms, a sleeve clasping the hand, wrist and forearm and a series of double and single element joints for establishing and maintaining control of gross and fine arm and hand movements in the cerebral palsy patient.

16 Claims, 8 Drawing Figures

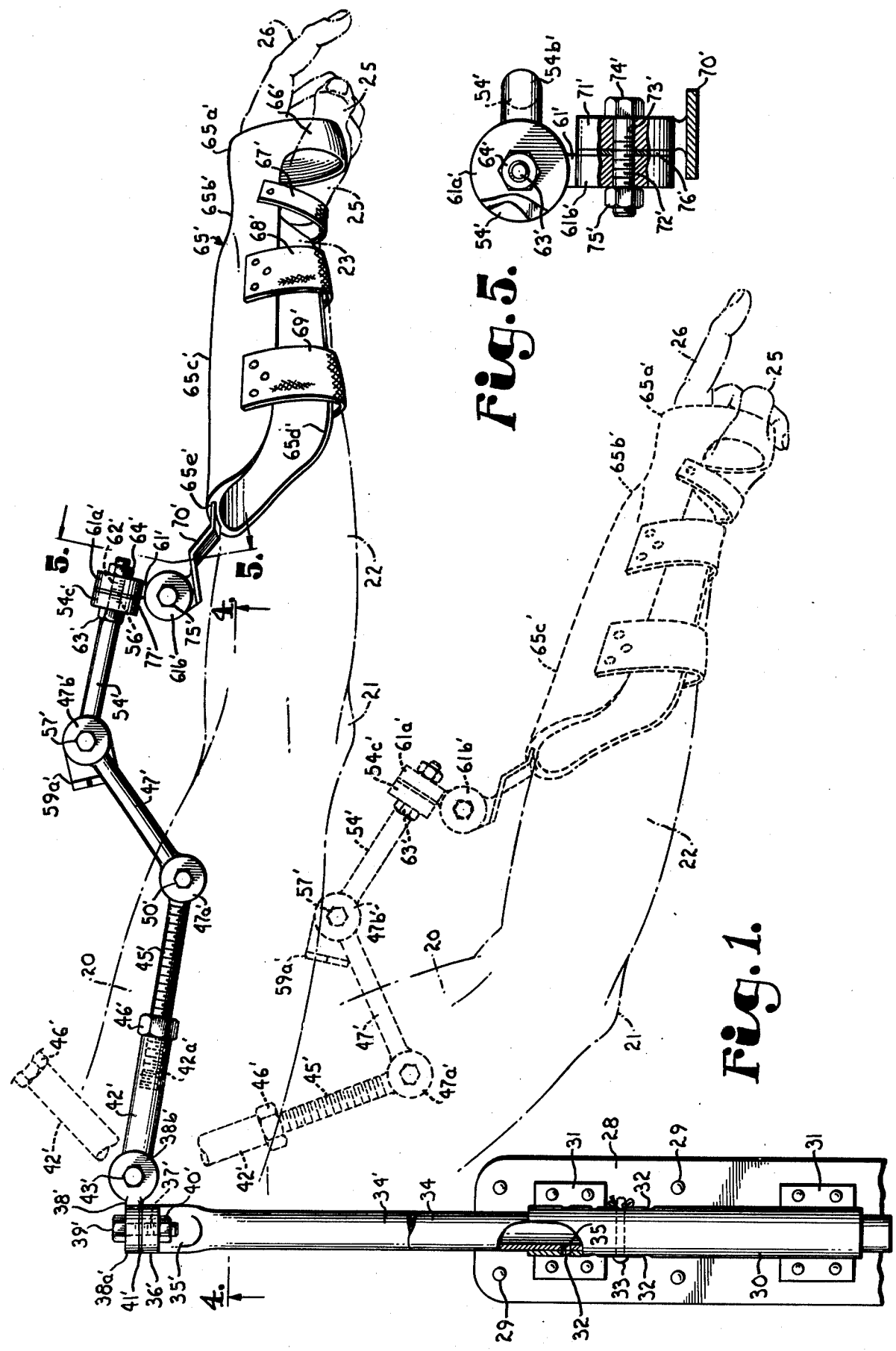

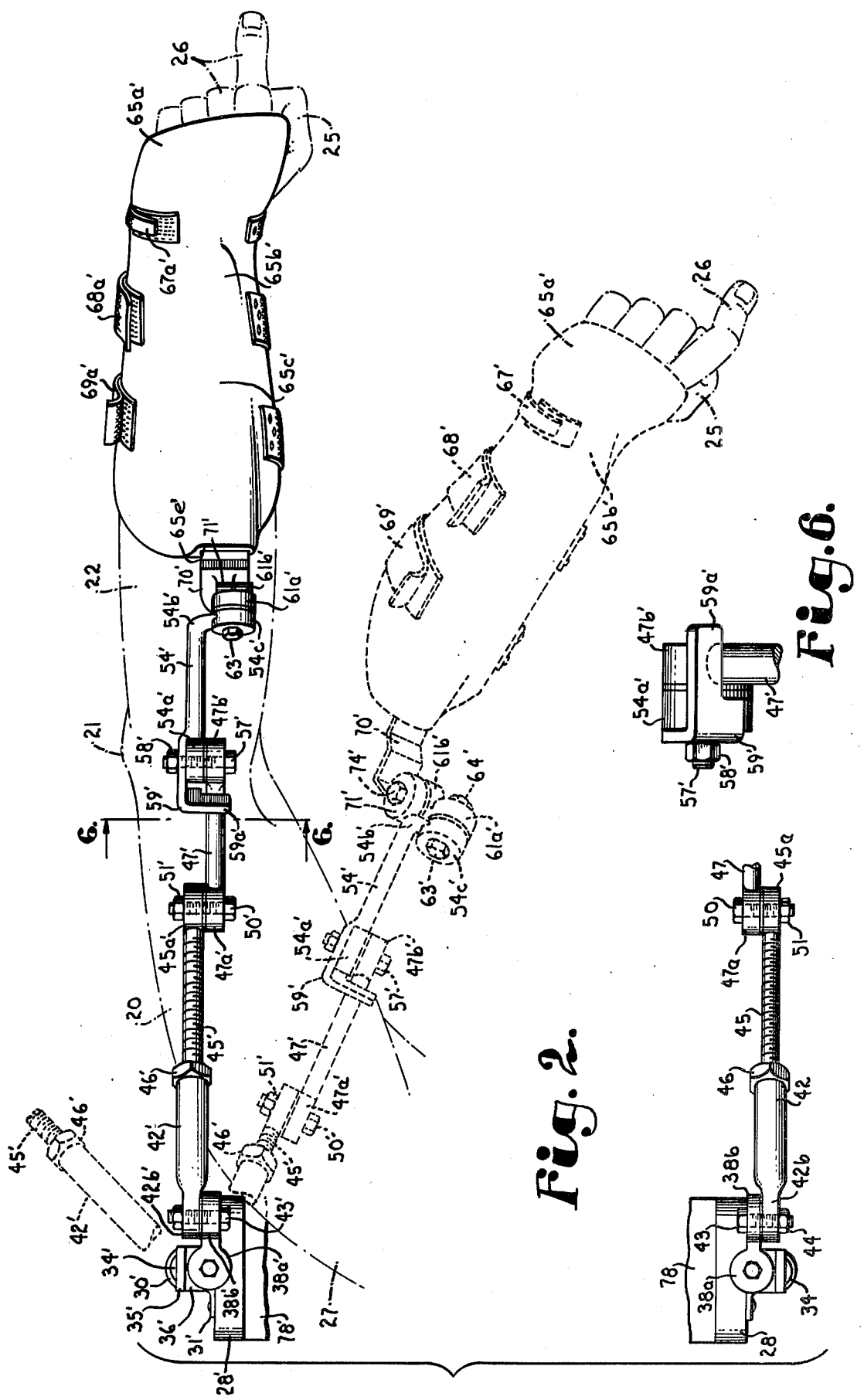

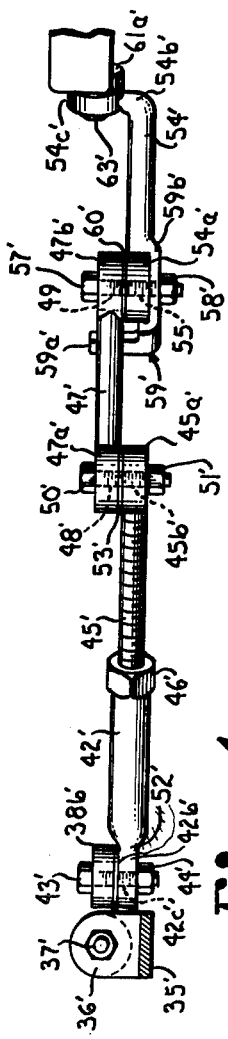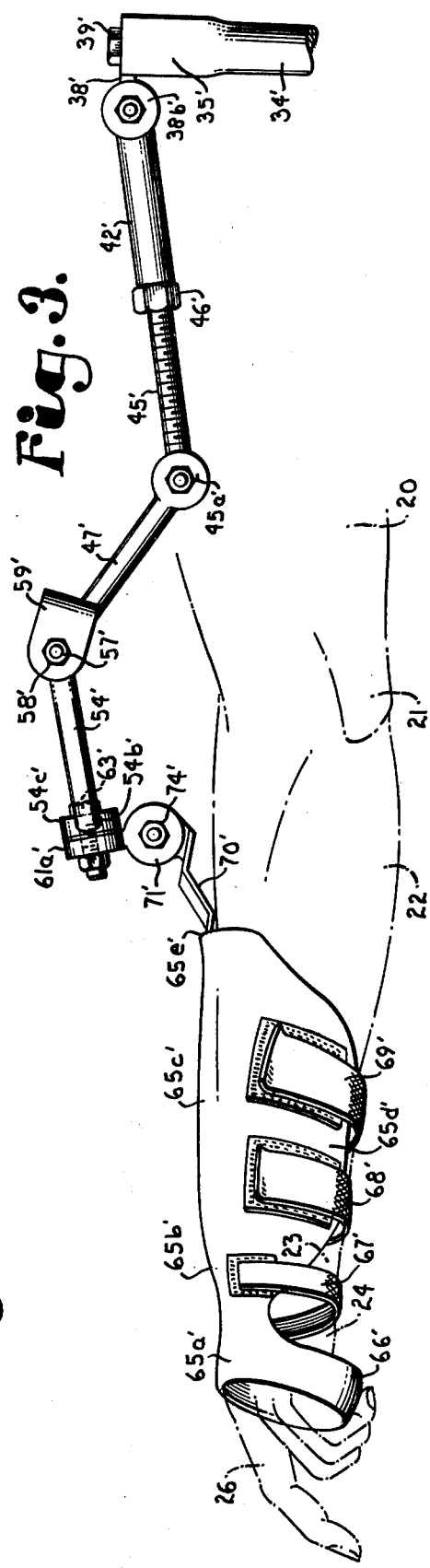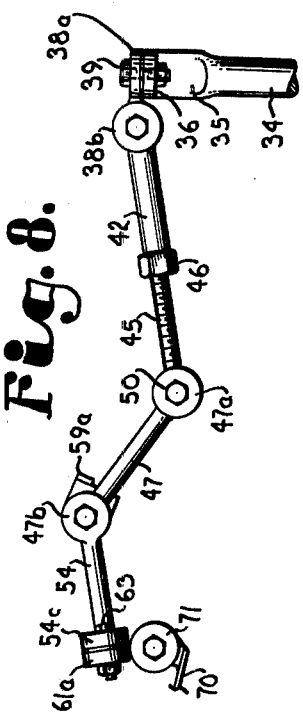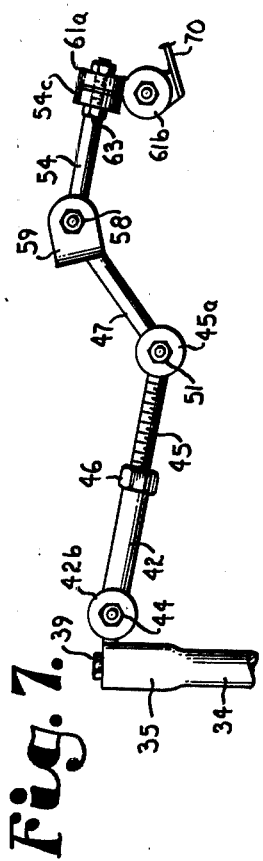

CEREBRAL PALSY ARM AND HAND BRACE

BACKGROUND OF THE INVENTION

The literature of cerebral palsy is voluminous. The instant invention is directed to certain specific problems arising out of certain manifestations of certain forms of cerebral palsy.

The latter is a condition primarily centered around paralysis, incoordination or weakness of the muscular system due to pathology of the motor control centers of the brain. Typically it is a term covering motor disabilities due to non-progressive brain pathology typically occurring in early life. With respect to causation, broad definitions speak of prenatal, natal and postnatal pathological processes having deleterious effects on the pyramidal, extra pyramidal or cerebellar systems. With respect to a classification of types, approaches involve (a) pathology, (b) the presenting clinical syndromes and (c) the regions of the body affected.

Five types are generally recognized in cerebral palsy, with varying degress and types of motor involvement: spastic, dyskinetic (including athetoid), ataxic, mixed and flaccid. The American Academy of Cerebral Palsy recognizes seven types: spastic, athetotic (tension, non-tension, dystonia and tremor athetosis), rigidity, ataxic, tremor, atonic and mixed. Speaking descriptively, the spastic type, comprising some 65% of the cerebral palsied, typically involves stiffness of musculature, with motions of the extremities made slowly and with great effort. Thus, when the afflicted person attempts to bend the joints, the opposing muscles contract, blocking the patient's efforts. In the athetoid type, typically comprising 30% of the afflicted, the individual moves his body or parts of his body even when he does not wish to. The body and extremities may be in constant motion. The individual may have difficulty in controlling and directing his movements. Phelps recognizes nine types of athetoids. These include rotary, dystonic, tremor-like, shudder-like, flail, non-tension, hemi-athetoid and emotional release athetosis.

In a classification based on neuromuscular characteristics, five types were distinguished, including spasticity, athetosis, tremor, rigidity and ataxia. With respect to the tremor syndrome, the muscles are typically normal in tone with no abnormal reflexes. The distinguishing characteristic is repetitive and rhythmic involuntary contractions of the flexor and extensor muscles. In the intentional sub-class, such are not present at rest and appear with voluntary or intended movement. In the non-intentional sub-class, such are present at rest and also continue with intended movement. Typically, these involuntary movements are fine and rhythmic, not gross and variable like the athetoid type. In the lower extremities, such tremors tend to throw the individual off balance. In the upper extremities, they interfere with hand skills and often may prevent development of writing skills and the like.

In therapy of cerebral palsy conditions, rests, body braces, special chairs and tables, corsets and other devices may be used to control those motions which use up much of the energy of cerebral palsied individuals. Motion training may also use such devices.

With respect to the philosophy of bracing and special equipment in treatment of cerebral palsy, the need arises from the disturbances of the neuromuscular function. There are differences of opinion with respect to the value of bracing and other special equipment in treatment. Some physicians value and some contraindicate. The purpose of use of such special equipment is to provide needed support, aid in control of involuntary movements, prevent or correct deformities and combinations of these.

In the literature, it is recognized that bracing and special equipment applied to the upper extremities is much less common. It is typically not needed for erect posture of the individual. To correct and prevent deformities of the upper extremities is very difficult. Many physicians consider it impractical to brace the shoulder and elbow joints. In such use, bracing of spastic hands is the most common type in order to counteract flexion deformities.

The previous ideas have been abstracted from the works of Allen, R. M. et al "Psychological Evaluation of the Cerebral Palsied Person" and McDonald, E. T. et al "Cerebral Palsy".

In Keats, Sidney "Cerebral Palsy", 1965, C. C. Thomas, Springfield, Ill., under Chapter V Modalities of Treatment, Subsection 6 Bracing, Page 236, there is first discussed foot, leg and back braces, particularly directed toward treatment of athetoid syndromes. Thereafter occurs a discussion of problems and efforts to control involuntary arm movement, such being devised according to the individual problem. Mentioned are spoon splints to prevent wrist flexion (which may extend to the forearm), hand sandwich braces to aid in controlling wrist and hand extension and forearm splint braces which may go above the elbow joint to maintain full or mid-suponated forearm position. Such may permit flexion and extension at the elbow joint with the forearm and hand in position of mid-suponation. It also may have a bar to prevent hand rotation through the wrist.

In Cruikshank, William N. (editor) "Cerebral Palsy, Its Individual And Community Problems", 1966, Syracuse University Press, Part C, Therapy and Education, Section VIII, Physical Therapy (Esther E. Snell), bracing is discussed at page 412 et seq. Such is discussed for support, the correction of deformities and control of extra motion. Materials are given typically as steel, aluminum and plastic. Parts mentioned are uprights, crossbands, joints, stops, cuffs, pelvic bands, gluteal pads, knee caps and knee pads. In joint classification, there are mentioned simple, box, ball bearing and spring joints.

Throughout these works, and in many others related, there runs the theme of non-intellectually impaired and often superiorly motivated individuals who are yet incapacitated to a greater or lesser degree (often greater) by their damaged motor nervous systems. Additionally, the frustration of inability to accurately and, with control, perform known, projected and willed acts for such people need not be described. It is this problem of furnishing specific means by which these physically handicapped individuals may capture or recapture neuromuscular function permitting them to do fine, controlled, willed work towards which this invention and application are directed. The purpose is to provide mechanical means by which the gross and fine action and function of the entire arm and hand complex may be stabilized and controlled; despite the presence of the previously incapacitating and disabling tremors. With this recovery or capturing of these crucial actions and functions, the afflicted individual is able to grasp an aspect of himself previously denied of the highest importance.

Additionally, therapy of these conditions is enabled to enter new realms previously denied it.

THE PRIOR ART

Applcant is aware of the following prior art U.S. Pat. Nos. directed to arm and hand splints and braces and joint constructions:

Maddox 1,340,630 "Arm Abduction Splint", issued May 18, 1920;

Lendinara 2,362,383 "Flexible Joints", issued Nov. 7, 1944;

Whitelaw 2,832,334 "Therapeutic Device. . . ", issued Apr. 29, 1958;

Keropian 3,707,963 "Articulated Hand Brace", issued Jan. 2, 1973.

Reference is also made to the Life Science Library work "The Engineer", by C. C. Furnas, et al, 1968 revision, Time-Life Books, New York City, N.Y., pages 162 and 163 with respect to the "Man Amplifier".

BRIEF DESCRIPTION OF THE INVENTION

Spasticity or spastic paralysis is generally regarded as a form of cerebral palsy. Cerebral palsy itself is broadly regarded as any non-progressive motor disorder typically caused by brain damage incurred during individual development. Thus, cerebral palsy is a non-specific term and typically includes many kinds of brain damage from various causes. Few authorities agree on the disorders to include.

In many forms or degrees of the neuro motor disorders labelled spasticity and spastic paralysis, willed movements of the entire arm, the upper arm, the forearm, hands and fingers are possible and feasible, but the effectiveness of such willed movements is vitiated and overshadowed by the presence of intermittent or continuous tremors or tremoring in the limbs and hands. What, then, is needed is a suitable brace or device which will clasp an arm or both arms in such a manner that the unwilled and undesired neuromuscular spasms and tremors will be damped and controlled, but the willed movements of the various arm and hand elements, gross and fine, not prevented.

The instant device has had remarkable success in stabilizing the said arm and hand tremors of individual suffering from spasticity and spastic paralysis, permitting them to feed themselves, typewrite, write, in short control their gross and fine arm and hand movements, specifically including:

(1) Complete shoulder articulation (up, down, sideways, arcuate, etc.);

(2) Flex and extend the forearm with respect to the upper arm at the elbow;

(3) Pronate and suponate the forearm; and (4) Brace the hand across the palm thereof in order to permit fine finger movements and actions.

One device for one arm or two devices for both arms may be connected to the back of a chair, to a wheel chair frame, or even to a back plate strapped to the individual themselves to provide mobile aid.

The instant device typically includes the following elements, working from the attachment on the chair, wheel chair, standing frame or back plate;

(1) A hollow sleeve adapted to removably receive and removably lock therewithin (by pins through the sleeve):

(2) The normally vertical shaft received within the said sleeve and pinned therein against rotational movement and vertical movement;

(3) A forearm clasping and hand encircling sleeve;

(4) A train of arms and articulating joints therebetween comprising:

(a) A double element joint adjacent the shoulder of the user;

(b) A single element inboard joint between the shoulder and elbow;

(c) A single element joint with an arm limitation (against excessive elbow extension) at the elbow; and (d) A double element joint just over the forearm past the elbow closely adjacent the inboard end of the sleeve.

A double element joint comprises two closely adjacent, right angle oriented sets of pinned, sliding, circular plates permitting multi-dimensional and multi-planar movement. A single element joint is one such set with movement limited to one plane.

The upper double element joint next the vertical shaft at the shoulder permits shoulder articulation; the two intermediate single element joints permit flexion and extension of a forearm with respect to the elbow (with extension limitation thereof); and the lower double element joint permits pronation and suponation of the forearm with respect to the elbow joint.

There is provided a frictional loading at each joint element which operate, jointly and severally, to damp the muscle spasms and neuro-muscular oscillations which are involuntary and unwilled. Variable resistance is provided at each joint element so that the entire train of joint elements is uniquely variably adjustable for given individual's problems. The frictional engagement is accomplished by tightening down the bolt engagement of each of the joint element face sets, with a threaded engagement and lock nut arrangement at each such joint element.

OBJECTS OF THE INVENTION

A first and primary object of the invention is to provide a device which will aid in stabilizing or, in fact, effectively so control or limit the arm tremors of spastic paralytics that they are able to feed themselves, move their arms and hands in a controlled manner, typewrite, write, in short, control their gross and fine arm movements.

Another object to the invention is to provide such an improved device for stabilizing the arm tremors of spastic paralytics which enables the afflicted person to perform:

(1) Complete shoulder articulation (up, down, sidewise, arcuate, etc.);

(2) Flexion and extension of the forearm with respect to the upper arm at the elbow; and (3) Pronation and suponation of the forearm. In addition, means are provided which enable the performance of fine finger movement in willed action and control.

Still another object of the invention is to provide an arm outlining frame which may be employed with one or both arms by an individual suffering from the uncontrollable tremors of spastic paralysis (one frame for each arm), which frame or frames articulate(s) in such manner as to permit all of the normal gross and fine upper arm, forearm and hand movements, yet simultaneously provides, with respect to each movement or pattern thereof, continuous, graded resistance at all times, so that, continuously, the entire arm structure of the afflicted individual is caged or controlled against the uncontrollable tremors or movements of the disease, yet may, by willed action, force gross and/or fine action through and against the frame.

Another object of the invention is to provide such an arm framing and engaging device of the character described which may be mounted on a vertical standing frame (for standup use), alternatively may be removably secured to a chair back (for sitting use) or, yet alternatively, may be secured to a frame strapped to the body of the user (for mobile use).

Yet another object of the invention is to provide such a device, of the character described, which device is extremely strong and rugged in use, of long life despite continuous and hard use, dependable in action and, finally, of a relative minimum of cost to fabricate. Yet further, all of the parts of the device are readily available for adjustment, replacement or repair.

Still another and further object of the invention is to provide an arm engaging and framing device of the character described, wherein a multiplicity of doubly and singly jointed arms connect a vertical post and a forearm engaging sleeve, there being a frictional loading at each joint element which operates to damp the muscle spasms and neuro-muscular oscillations of the afflicted individual, the frictional loading and engagement at each joint element being individually variable and adjustable.

Still another object of the invention is to provide a multiply jointed, articulated frame for use in a device of the character described wherein, as mentioned, there is a frictional loading at each joint element. Despite this fact and despite the fact that the device will typically be used for many years with all the joints being exercised, in every way possible, the joint element construction is such that no substantial wear or deterioration of any of the joint elements will occur over the years and the infinite variability of adjustment of each joint element will not deteriorate from use or aging.

Yet another object of the invention is to provide such a device, frame and articulation thereof, as well as structural configuration, wherein an absolute minimum of maintenance and repair will be required over the years and such daily or periodic adjustment of joint frictional loadings as may be required is readily and easily made, without any difficulty and with constant full access to every joint element.

Other and further objects will appear in the course of the following description of the invention.

In the drawings, which form a part of the instant specification and are to be read in conjunction therewith, embodiments of the invention are shown and, in the various views, like numerals are employed to indicate like parts.

FIG. 1 is a composite side view showing, in the center and right hand portions of the view, the subject stabilizing device as applied to the left arm of a user. In full lines, the user's left arm is shown essentially fully extended and neither pronated nor suponated. In the dotted line showing of FIG. 1 below the full line showing, the user's left arm is shown somewhat flexed toward himself and, additionally, somewhat pronated from the full line showing. In the lower left hand portion of FIG. 1, the mounting for the device for the user's right hand arm is seen. In the upper left hand portion of FIG. 1, in dotted lines, the inboard portion of the frame is shown rotated upwardly (fragmentarily).

FIG. 2 is a composite top view of the apparatus of FIG. 1, with the upper and center portions of FIG. 2 in full and dotted line showings corresponding to the full and dotted line showings of FIG. 1. In the lower left hand portion of FIG. 2, the mounting for a right arm device is shown (jibing with the showing with the mounting in the lower left hand portion of FIG. 1). In the upper left hand portion of FIG. 2, the inboard portion of the frame is shown (dotted lines) with the arm moved outwardly to the left.

FIG. 3 is a side view of the left arm stabilizing frame and device of FIGS. 1 and 2 seen from the opposite side of the full line showing of FIG. 1.

FIG. 4 is a view taken along the line 4—4 of FIG. 1 in the direction of the arrows.

FIG. 5 is a view taken along the line 5—5 of FIG. 1 in the direction of the arrows.

FIG. 6 is a view taken along the line 6—6 of FIG. 2 in the direction of the arrows.

FIG. 7 is a fragmentary side view of the right arm stabilizing device oriented parallel to the full line showing of the left arm stabilizing device in FIG. 1 as seen therein in full lines.

FIG. 8 is a fragmentary side view of the opposite side of the device of FIG. 7.

STRUCTURE AND FUNCTION

Turning to the Figures, the device in question will now be described in detail and its structure and function set forth. In FIGS. 1, 2 and 3, there is seen the upper arm 20, the elbow joint 21, the forearm 22, the wrist 23 and hand 24 of the user of the device. Yet further, in this representation on the left arm and hand of the user, there is seen his thumb 25 and fingers 26. In the left hand portion of FIG. 2, the individual's upper arm or shoulder joint region is seen at 27.

The fundamental base or support construction mounting the entire apparatus to be described is best seen in the lower left hand corner of FIG. 1. This comprises a plate 28, which may be attached (typically, but not limiting) to the back of a chair, to a wheelchair frame, or even to a back plate strapped to the individual himself. Suitable bolt, screw or rivet holes 29 are shown on plate 28 for conventional attachment to an underlying support construction. Yet another method of mounting the apparatus to be described and the plate 28 supporting same could comprise vertical beams or a vertical frame fixed adjacent to a place of work, such as workbench or the like.

A hollow cylindrical sleeve 30 is fixedly attached to or gripped upon plate 28 by conventional means such as brackets 31. The orientation of plate or plates 28 (two such would be employed, one on each side of the individual, where both arms of the individual were to be coupled with subject devices) is preferably, but not necessarily, substantially vertical so that the orientation of hollow cylindrical sleeve 30 is also preferably (not necessarily) substantially vertical. Vertically spaced sets of opposed openings 32 are provided in sleeve 30, to receive therethrough one or more pins 33. Pins 33 serve to fix the vertical and rotational position of cylindrical tube or shaft 34 which is removably receivable within sleeve 30. Shaft 34 has one or more sets of oppositely matched, opposed perforations or openings 35 in wall thereof adapted to align with openings 32 in sleeve 30. Both the sleeve 30 and the shaft 34 may be square, hexagonal, etc. in transverse horizontal section (in the view of FIG. 1), if desired, but circular section is easiest. Height adjustment of the top of shaft 34 with respect to plate 28 is provided by the multiplicity of openings 32 in (2) the normally vertical shaft 34' received within the said sleeve 30' and pinned therein against rotational movement and vertical movement;

(3) the forearm clasping and hand encircling sleeve member 65';

(4) a train of arms and articulating joints therebetween comprising:

(a) a double element joint adjacent the shoulder of the user between shaft 34' and arm 42';

(b) a single element inboard joint between the shoulder and elbow established between rods or arms 45' and 47';

(c) a single element joint with an arm limitation (member 59' against excessive elbow extension) at the elbow between rods or arms 47' and 54'; and (d) a double element joint just over the forearm past the elbow adjacent the inboard end of the sleeve between rod 54' and configured flange 70'.

A double element joint, as above described, comprises two closely adjacent, right angle oriented sets of pinned, sliding, circular plates which, together, permit multi-dimensional and multi-planar movement. A single element joint is one such set with movement limited to a single spatial plane. Thus, the double element joint next normally vertical shaft 34' at the user's shoulder permits shoulder articulation. The two, intermediate, single element joints connecting rods 45', 47' and 54' permit flexion and extension of the forearm with respect to the elbow (with extension limitation thereof). The outermost double element joint, between rod 54' and flange 70', permits pronation and suponation of the forearm with respect to the elbow joint of the user.

The provision of the circular or disk-like elements in the said joints, with the threading of one of the disk-like elements and optional washer, together with the lock nut, permit a graded, fixed, tightening or tension at each joint which provides a variable (yet fixed for a given setting) frictional loading at each joint element. These frictional loadings at each joint element, which may be different from joint connection to joint connection, operate, jointly and severally, to damp the muscular spasms and neuro-muscular oscillations of the user which, in spastic paralysis, are involuntary and unwilled. The variable (yet fixed at a given setting) resistance provided at each joint element permits the entire train of joint elements, jointly and severally, to be uniquely and variably settable or adjustable for a given individual's problems. The desired frictional engagement for a given joint element connection (bolt through two facing disk elements) is accomplished by tightening down the bolt engagement of each of the joint element facing sets to the desired tension, with the lock nuts on the free end of the bolt fixing the setting at that tension for each such joint element.

The instant device or apparatus thus comprises a neuromuscular stabilizing device for the human arm and hand which comprises, in combination, (1) a normally vertical support post or arm 34' having normally upper and lower ends, (2) a sleeve adapted to embrace a human forearm which has an inboard end (towards the elbow) and outboard end (toward the hand) and (3) an articulated linkage chain which couples together the upper end of the support post and the inboard end of the sleeve. The said articulated linkage chain includes the following elements. A first arm 42', having inboard and outboard ends, is connected to the upper end of the post 34' at its inboard end, the means connecting the said post and first arm comprising a double element friction joint. The said first arm may be length adjustable, as provided by the threaded extension thereof 45'. A second arm 47', also having inboard and outboard ends, is coupled at its inboard end to the outboard end of the extension 45' of the first arm 42'. The means which couples the said first and second arms comprises a single element friction joint. A third arm 54', also having inboard and outboard ends, is coupled at its inboard end to the outboard end of the second arm 47'. The means coupling the arm 54' to arm 47' comprises a single element friction joint, in this case also having extension limiting means in one direction, specifically member 59'. The outboard end of arm 54' is coupled to sleeve 65' at the inboard end of the latter, via flange 70' connected thereto. The means coupling the outboard end of arm 54' with the inboard end of the sleeve comprises a double element friction joint.

Each of the joint elements described includes a pair of disk-like or circular facing elements having each a central hole therethrough, with one of the circular facing elements having the hole therethrough internally threaded. A threaded bolt engages the two circular facing elements and is threaded into the said one element, with a lock nut threaded on the free end of the bolt. A frictional washer may be provided between the pair of circular or disk-like facing elements.

USE AND APPLICATION

As previously mentioned, the subject device may be mounted, in single or dual arm application, on a chair, a wheelchair, a vertical standing frame or on a body harness. All that is needed is an essentially vertical mounting of one or more plates 28 on such a chair back, frame, body harness or the like, immediately outside the position of the shoulder joints of the individual and therebelow, whereby the tops of the shafts or rods 34 and 34' will be at or opposite the top of the shoulder level of the individual when he is seated in the chair, standing within the work frame or has the body harness mounted on him.

The next adjustment is to so thread rods 45 and 45' into hollow shafts 42 and 42' that, when the individual's hand, wrist and forearm are clasped by the sleeves 65 and 65' as seen in the drawings, the single joints (single element joints) between rod 45' (45) and rod 47' (47) are above the elbow joints, the double element joints between rods 54 and 54' and flanges 70 and 70' are below the elbow joints and the single element joints (with extension limitation) between rods 47 and 47' and rods 54 and 54' are substantially aligned with the elbow joints of the user. This is the arrangement seen in full lines in FIGS. 1 and 2.

Even with the user's arm fully extended, the rods 47 and 54 are angled with respect to one another with the single element joint therebetween above the joints thereabove and therebelow. This permits the further straightening out of the entire frame when it is desired to remove the arm, forearm, hand, etc. from the clasp of the given frame. Additionally, this arrangement ensures that, when the arm of the user is lowered and/or bent at the elbow, the joint action is as seen in the dotted line showing of FIG. 1, specifically, the single element joint between rods 47' and 54' remains above the joints on either side thereof in the train of articulated elements.

Depending upon the disability pattern (types, amplitudes, distributions and magnitudes of tremoring) in the individual, the train of joints is adjusted to provide the desired resistance at each element. This may be readjusted, from time to time, as changes may take place in the nervous system of the individual from regaining control or as fatigue sets in, as muscular development occurs from use, as learning and skill are achieved, etc.

Before the forearm, wrist and hand are engaged or disengaged, the straps 67-69, inclusive are unsnapped or disengaged, to be engaged at the desired tension, once the hand, wrist and forearm are inserted into the sleeve and hand engaging structure.

From the foregoing, it will be seen that this invention is one well adapted to attain all of the ends and objects hereinabove set forth together with other advantages which are obvious and which are inherent to the process.

It will be understood that certain apparatus features, structures and sub-combinations thereof are of utility and may be employed without reference to other features, structures and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

We claim:

1. A neuro-muscular stabilizing device for the human arm and hand comprising, in combination,
   a normally vertical post having normally upper and lower ends,
   a sleeve adapted to embrace a human forearm having an inboard end (towards the elbow) and an outboard end (towards the hand), and a linkage means coupling together the upper end of the post and the inboard end of the sleeve comprising:
   (a) a first arm having inboard and outboard ends connected to the upper end of the post at its inboard end,
   (b) the means connecting the said post and first arm comprising a double element friction joint,
   (c) a second arm having inboard and outboard ends coupled at its inboard end to the outboard end of the first arm,
   (d) the means coupling the first and second arms comprising a single element friction joint,
   (e) a third arm having inboard and outboard ends coupled at its inboard end to the outboard end of the second arm,
   (f) the means coupling the third arm to the second comprising a single element friction joint having extension limiting means in one direction, and
   (g) means coupling the outboard end of the third arm with the inboard end of the sleeve comprising a double element friction joint.

2. A device as in claim 1 wherein each joint element includes a pair of circular facing elements having each a central hole therethrough, one of the circular facing elements having the hole therethrough internally threaded,
   a threaded bolt engaging the two circular facing elements and threaded into the said one element, and
   a lock nut threaded on the end of the bolt.

3. A device as in claim 1 wherein the extension limiting means in one direction on the single element friction joint coupling the third arm to the second arm comprises a plate fixed to the inboard end of the third arm which has a portion thereof overlying the outboard end of the second arm.

4. A device as in claim 1 including means for adjusting the length of the first arm, wherein the first arm is length adjustable.

5. A device as in claim 4 wherein the first arm is made up of two parts, the first part being hollow and internally threaded, the second part being an externally threaded rod threadably engaged with the first part and a lock nut on the second part to fix the length adjustment.

6. A device as in claim 1 including socket means receiving said normally vertical post and means for fixing said normally vertical post in said socket.

7. A device as in claim 1 wherein each double element friction joint comprises a pair of closely adjacent, connected, right angle oriented sets of paired, circular facing elements,
   each pair of circular facing elements having each a central hole therethrough, one of the said elements having the hole therethrough internally threaded,
   a threaded bolt engaging the two circular facing elements of each said pair and threaded into the one said element, and
   a lock nut threaded on the end of the bolt.

8. A neuro-muscular stabilizing device for a human arm comprising, in combination:
   a normally vertical post having normally upper and lower ends,
   an elongate, substantially rigid sleeve adapted to embrace a human forearm having an inboard end (towards the elbow) an outboard end (toward the hand),
   a coupling linkage train connecting the upper end of the post and the inboard end of said sleeve, comprising:
   (a) a first arm having inboard and outboard ends connected to the upper end of the post at its inboard end,
   (b) the means connecting the said post and first arm comprising a double element friction joint,
   (c) another arm having inboard and outboard ends coupled at its outboard end to the inboard end of the sleeve,
   (d) the means coupling the outboard end of the said other arm and the inboard end of the sleeve comprising a double element friction joint, and
   (e) means coupling the inboard end of the other arm and the outboard end of the first arm to one another, the said means coupling together the inboard end of the other arm and the outboard end of the first arm including a pair of single element friction joints oriented in substantially the same plane.

9. A device as in claim 8 wherein one of said single element friction joints has extension limiting means in one direction associated therewith.

10. A device as in claim 8 wherein each joint element includes a pair of circular facing elements having each a central hole therethrough, one of the circular facing elements having the hole therethrough internally threaded,
    a threaded bolt engaging the two circular facing elements and threaded into the said one element, and
    a lock nut threaded on the end of the bolt.

11. A device as in claim 8 wherein each double element friction joint comprises a pair of closely adjacent, connected, right angle oriented sets of paired circular facing elements, each pair of circular facing elements having each a central hole therethrough, one of the said elements having the hole therethrough internally threaded, a threaded bolt engaging the two circular facing elements of each said pair and threaded into the one said element, and a lock nut threaded on the end of the bolt.

12. A device as in claim 8 including means for adjusting the lengths of the first arm, wherein the first arm is length adjustable.

13. A device as in claim 12 wherein the first arm is made up of two parts, the first part being hollow and internally threaded, the second part being an externally threaded rod threadably engaged with the said first part and a lock nut on the second part to fix the length adjustment.

14. A device as in claim 8 including socket means receiving said normally vertical post and means for fixing said normally vertical post in said socket.

15. A neuro-muscular stabilizing device for the human arms and hands comprising, in combination, a pair of normally vertical posts having normally upper and lower ends, a pair of opposed sleeves, one associated with each said post, said sleeves adapted to embrace the left and right hand human forearms, respectively, each said sleeve adapted to embrace the human forearm having an inboard end (toward the elbow) and an outboard end (towards the hand), and a linkage means coupling together the upper end of each one of said posts and the inboard end of each respective sleeve, comprising:

(a) a first arm having inboard and outboard ends connected to the upper end of the post at its inboard end, (b) the means connecting the said post and first arm comprising a double element friction joint, (c) a second arm having inboard and outboard ends coupled at its inboard end to the outboard end of the first arm, (d) the means coupling the first and second arms comprising a single element friction joint, (e) a third arm having inboard and outboard ends coupled at its inboard end to the outboard end of the second arm, (f) the means coupling the third arm to the second comprising a single element friction joint having extension limiting means in one direction, and (g) means coupling the outboard end of the third arm with the inboard end of the sleeve comprising a double element friction joint.

16. A neuro-muscular stabilizing device for the human arms and hands comprising, in combination, a pair of normally vertical posts having normally upper and lower ends, a pair of opposed sleeves, one associated with each said post, said sleeves adapted to embrace the left and right hand human forearms, respectively, each said sleeve adapted to embrace the human forearm having an inboard end (toward the elbow) and an outboard end (toward the hand), and a coupling linkage train connecting the upper end of each respective post and the inboard end of the sleeve associated therewith, said train comprising, in each case:

(a) a first arm having inboard and outboard ends connected to the upper end of the post at its inboard end, (b) the means connecting the said post and first arm comprising a double element friction joint, (c) another arm having inboard and outboard ends coupled at its outboard end to the inboard end of the sleeve, (d) the means coupling the outboard end of said other arm and the inboard end of the sleeve comprising a double element friction joint, and (e) means coupling the inboard end of the other arm and the outboard end of the first arm to one another, said means coupling together the inboard end of the other arm and the outboard end of the first arm including a pair of single element friction joints oriented in substantially the same plane.

* * * * *